United States Patent [19]

Bisha

[11] Patent Number: 4,689,043

[45] Date of Patent: Aug. 25, 1987

[54] IV TUBE ACTIVATOR

[75] Inventor: Jon Bisha, Coronado, Calif.

[73] Assignee: IMED Corporation, San Diego, Calif.

[21] Appl. No.: 841,402

[22] Filed: Mar. 19, 1986

[51] Int. Cl.$^4$ .................. A61M 5/005; A61M 5/165
[52] U.S. Cl. .................................. 604/250; 604/249; 604/251; 128/DIG. 13
[58] Field of Search ............. 604/250, 245, 251, 253, 604/254, 255, 249; 128/DIG. 13

[56] References Cited

U.S. PATENT DOCUMENTS

| | | | |
|---|---|---|---|
| 2,715,905 | 8/1955 | Ogle | 128/214 |
| 2,775,240 | 12/1956 | Morrisey, Jr. et al. | 128/214 |
| 2,889,848 | 6/1959 | Redmer | 137/315 |
| 3,189,038 | 6/1965 | von Pechmann | 137/315 |
| 3,216,418 | 11/1965 | Scislowicz | 128/214 |
| 3,316,935 | 5/1967 | Kaiser et al. | 137/595 |
| 4,142,524 | 3/1979 | Jassawalls et al. | 128/214 |
| 4,155,362 | 5/1979 | Jess | 128/214 F |
| 4,187,057 | 2/1980 | Xanthopoulos | 417/63 |
| 4,230,151 | 10/1980 | Jonsson | 137/595 |
| 4,407,434 | 10/1983 | Kempf | 222/214 |
| 4,411,652 | 10/1983 | Kramer et al. | 604/153 |
| 4,439,179 | 3/1984 | Lueders et al. | 604/34 |
| 4,460,358 | 7/1984 | Somerville et al. | 604/250 |
| 4,524,802 | 6/1985 | Lawrence et al. | 137/595 |
| 4,586,691 | 5/1986 | Kozlow | 251/7 |

Primary Examiner—C. Fred Rosenbaum
Assistant Examiner—Gene B. Kartchner
Attorney, Agent, or Firm—Workman, Nydegger & Jensen

[57] ABSTRACT

An IV tube activator for use with a peristaltic IV infusion pump comprises means that require the closure of a tube associated clamp upon engagement of the IV tube with the pump and upon any subsequent disengagement of the IV tube from the pump. The activator further comprises means which simultaneously move the tube associated clamp to open the IV tube when the pump is being operated.

9 Claims, 11 Drawing Figures

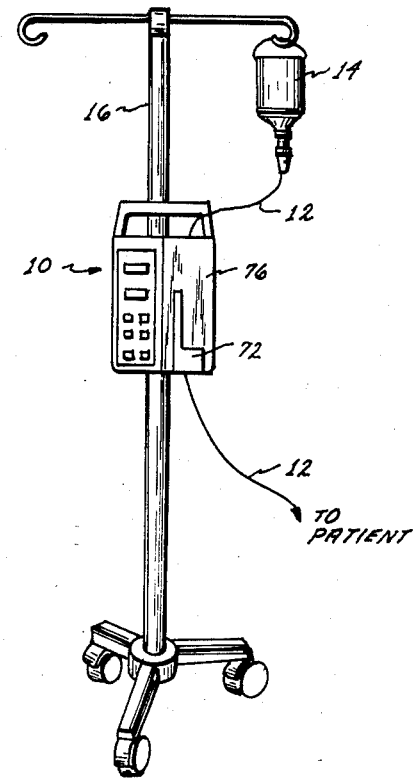
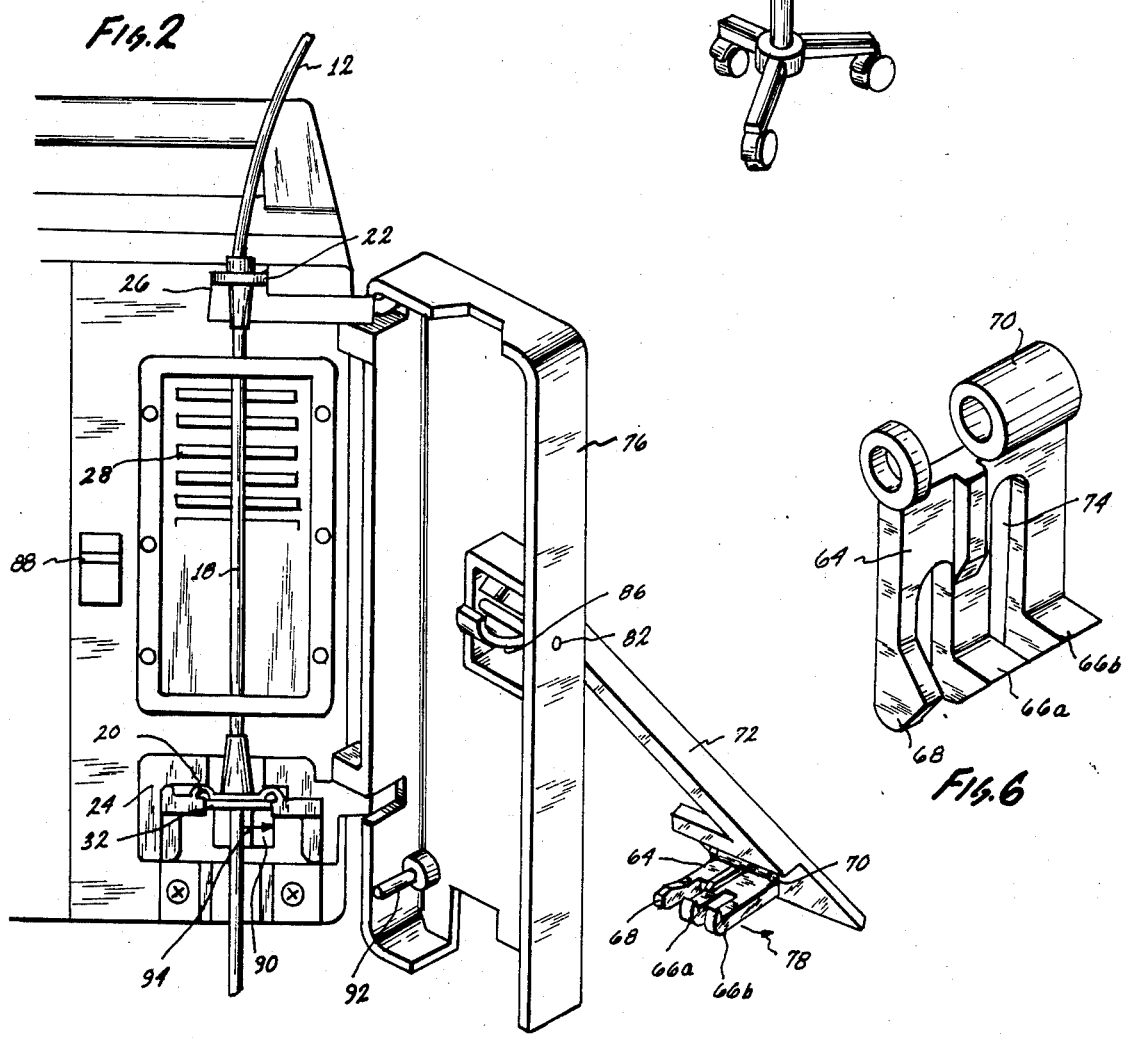

IV TUBE ACTIVATOR

BACKGROUND OF THE INVENTION

This invention relates generally to slide clamps used to control fluid flow through an IV line. More specifically, the present invention relates to an apparatus which requires structural cooperation between the slide clamp and an IV infusion medical device for activation and deactivation of the clamp on the IV line. The present invention is particularly, though not exclusively, useful for the operative engagement and subsequent safe disengagement between an IV line and a linear peristaltic IV infusion pump.

DESCRIPTION OF THE PRIOR ART

The use of medical devices for the IV infusion of medical solutions to patients is well known in the medical professions. One type of medical device which has been widely used for this purpose is the peristaltic pump. As is well known in the pertinent art, peristaltic pumps create a moving zone of occlusion along a portion of the IV line to create the pumping action required. However, because they require a patent IV tube for their operation, when the tube is not engaged with the pump, there is the danger of possible unwanted free flow of medical solution from the fluid source directly into the patient. Typically, the times of greatest concern for this danger are during the initial set-up of the IV administration system and at any subsequent times when the IV line is connected between the fluid source and the patient and becomes, for whatever reason, disengaged from the device.

The control of fluid flow through patent IV lines from a fluid source to a patient is an ever present problem and several devices to help solve this problem have been proposed. For example, slide clamps which constrict or obstruct the IV line are well known. Typically, these are manually operated clamps which are found in various configurations. One such clamp is a roller clamp of the type described in U.S. Pat. No. 3,189,038 to Von Pechmann. Another type is the well-known slide clamp, an example of which is disclosed in U.S. Pat. No. 2,889,848 to Redmer. Again, such clamps are manually operated. Further, they must be activated independently and separately from any medical device which may be operatively attached to the IV fluid line.

In situations where a medical device is to be used for the infusion of medical solutions to a patient, it is necessary to coordinate the use of a tube clamp with the operation of the device. For reasons given above, this is particularly so where a peristaltic pump is used. The idea of associating the clamp with the device to bring about a cooperation of structure therebetween is known in the prior art. For example, the invention disclosed in pending application Ser. No. 733,667 to Kozlow, now U.S. Pat. No. 4,586,691, which is assigned to the assignee of the present invention, discloses a safety slide clamp which requires the cooperation of structure between the device and the clamp itself. Such a clamp as disclosed in the Kozlow application, however, requires manual activation of the clamp to open the tube prior to the actual operation of the pump. Although such a clamp may be acceptable in some cases, in others the additional manipulation required to activate the clamp may be inconvenient or undesirable.

In light of the above, it can be appreciated that there is a need to simplify the engagement of an IV tube with a peristaltic infusion device. Specifically, there is a need to reduce the number of steps necessary to accomplish such an engagement. Thus, there is a need for a clamping apparatus which eliminates the manual step of activating the tube clamp.

Accordingly, it is an object of the present invention to provide a clamp activation apparatus which ensures safe operation of a peristaltic infusion device. It is another object of the present invention to provide a means which ensures that only a restricted or obstructed IV tube can be engaged with a peristaltic device. Further, it is an object of this invention to provide a device which prevents removal of a patent tube from the device. It is yet another object of the present invention to provide an apparatus which automatically makes the tube patent while simultaneously preparing the device for its operation.

SUMMARY OF THE INVENTION

The activation apparatus of the present invention provides for the activation of an IV tube associated slide clamp through the operation of structural components of an IV infusion medical device. The present invention includes means for holding the IV tube in operative engagement with the device while a handle which is pivotally mounted on the device is allowed to move into engagement with the clamp. The handle is structured to urge the clamp from a closed position, wherein the clamp constricts or restricts the flow of fluid through the tube, to an open position wherein the tube is patent. The handle also includes structure to operate reversibly and urge the clamp from the open position to the closed position in preparation for the removal of the tube from the device. The apparatus of the present invention also comprises a lockout means which is mounted on the device to ensure that initial engagement of the IV tube with the device can only be accomplished when the clamp is in the closed position.

The novel features of this invention as well as the invention itself, both as to its organization and operation, will be best understood from the accompanying drawings taken in conjunction with the accompanying description in which similar reference characters refer to similar parts and in which:

BRIEF DESCRIPTION OF THE DRAWINGS

FIG. 1 is an elevation view of a peristaltic device incorporating the present invention in operable engagement with an IV tube;

FIG. 2 is an elevation view of an IV tube in engagement with a linear peristaltic pump with various components disengaged from one other;

FIG. 6 is a perspective view of the grip of the present invention;

DESCRIPTION OF THE PREFERRED EMBODIMENT

Figure 3A:
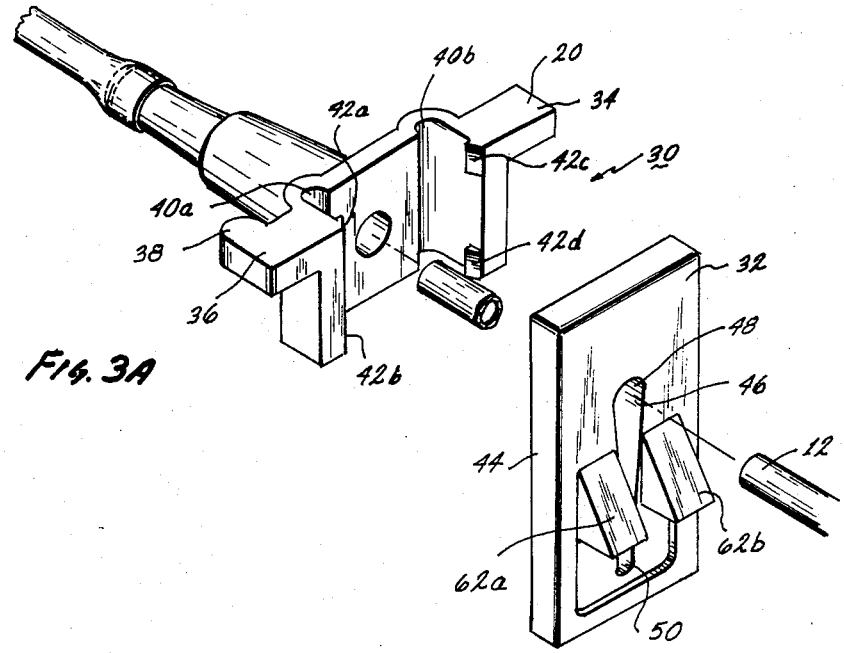
FIG. 3A is an exploded perspective view of the slide clamp assembly with portions broken away for clarification.

The intended environment for the present invention is best seen in FIG. 1 where a peristaltic infusion device, generally designated 10, is shown in operative engagement with an IV tube 12. In FIG. 1, it is seen that a fluid source 14 can be suspended from appropriate apparatus associated with an IV pole 16 and IV tube 12 connected for fluid communication between fluid source 14 with a patient (not shown).

Referring now to FIG. 2, it is seen that IV tube 12 includes a pumping section 18 made from any appropriate elastomeric material which will permit an effective peristaltic action on the pumping section 18. One end of pumping section 18 is connected into fluid communication with IV tube 12 by a fitment 22. A slide clamp fitment 20 connects the other end of pumping section 18 with a continuation of IV tube 12. With therse connections, a continuous fluid path is provided through IV tube 12 and its associated pumping section 18.

As shown in FIG. 2, IV tube 12 and its associated pumping section 18 are mounted on the device 10 by the engagement of fitment 22 with upper bracket 26 and the engagement of slide clamp fitment 20 with lower hinge bracket 24. Thus, when IV tube 12 is engaged with device 10, pumping section 18 is positioned against the peristaltic pumping means 28. Also, with this engagement, pumping section 18 is placed under slight tension to ensure a snug fit between pumping section 18 and the peristaltic device 10. The connection of fitment 22 between IV tube 12 and pumping section 18 can be accomplished by any means well known in the art, such as solvent bonding. Likewise, the connection between slide clamp fitment 20 and pumping section 18 and IV tube 12 can be accomplished by any means well known in the pertinent art.

Figure 4:
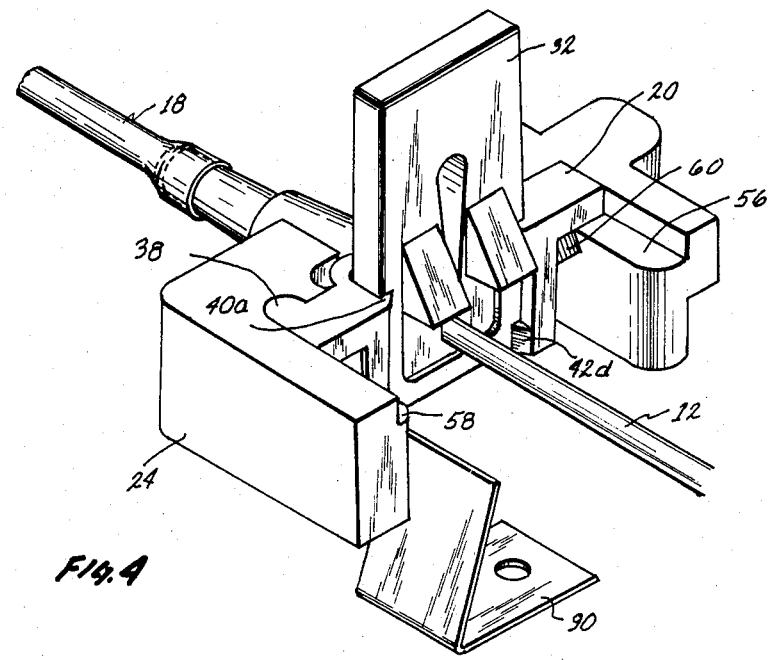
FIG. 4 is a perspective view of the slide clamp assembly nested in the lower hinge bracket with the slide clamp in a tube constricting position.
Figure 5:
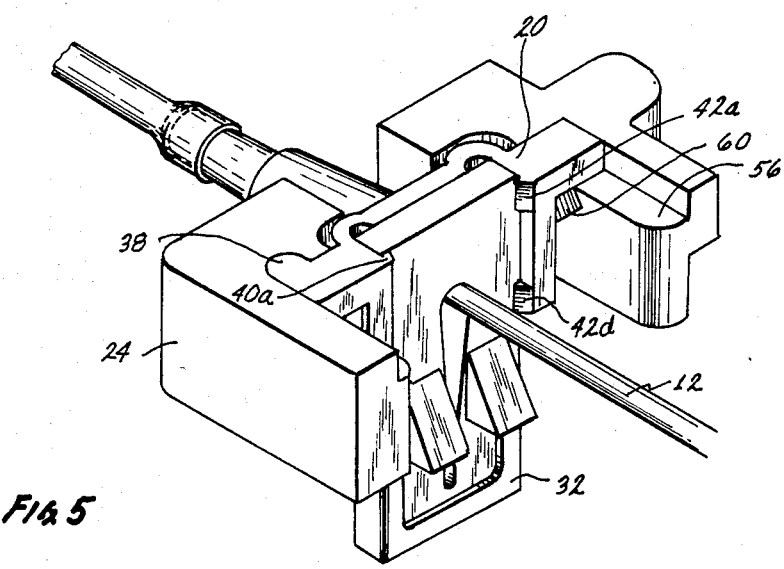
FIG. 5 is a perspective view of the slide clamp assembly nested in the lower hinge bracket with the slide clamp in a tube open position.

FIG. 3A shows an exploded perspective view of the slide clamp assembly for the present invention, generally designated 30. As shown, slide clamp assembly 30 includes slide clamp fitment 20 which is formed with a tab 34 and a tab 36. Further, tab 36 is formed with a key 38. Slide clamp fitment 20 is also formed with guides 40a and 40b and with retaining snaps 42a, b, c and d. The retaining snaps 42a, b, c and d allow for a snap fit engagement of the slide clamp 32 with slide clamp fitment 20 into a structure which is best seen in FIGS. 4 and 5. Further, the engagement of slide clamp 32 with slide clamp fitment 20, which permits the sliding of clamp 32 relative to fitment 20, is restrained by the mating engagement of ridges 44 with guides 40a and 40b. Although not shown specifically in FIG. 3A, it can be appreciated that ridges 44 are formed around the periphery of slide clamp 32 simply by forming a depression on the surface of slide clamp 32 (depression not shown in FIG. 3A).

In light of the foregoing, and since IV tube 12 is fixedly attached to slide clamp fitment 20, the engagement of slide clamp 32 with slide clamp fitment 20 allows for reciprocal motion of the slide clamp 32 relative to IV tube 12. Accordingly, this motion will cause either a patent IV tube 12 or a restricted IV tube 12. More specifically, by positioning clamp 32 relative to IV tube 12 so that IV tube 12 is in the enlarged portion 48 of aperture 46, a patent IV tube 12 is obtained. Subsequently, IV tube 12 can be restricted by moving slide clamp 32 relative to IV tube 12 so as to position IV tube 12 within the slotted portion 50 of aperture 46 when it is desired to restrict or occlude IV tube 12. Reference to FIG. 4 and FIG. 5 shows the positioning of slide clamp 32 relative to IV tube 12 and its respective positioning relative to slide clamp fitment 20 when the slide clamp 32 occludes IV tube 12 and when slide clamp 32 allows fluid flow through IV tube 12.

Figure 3B:
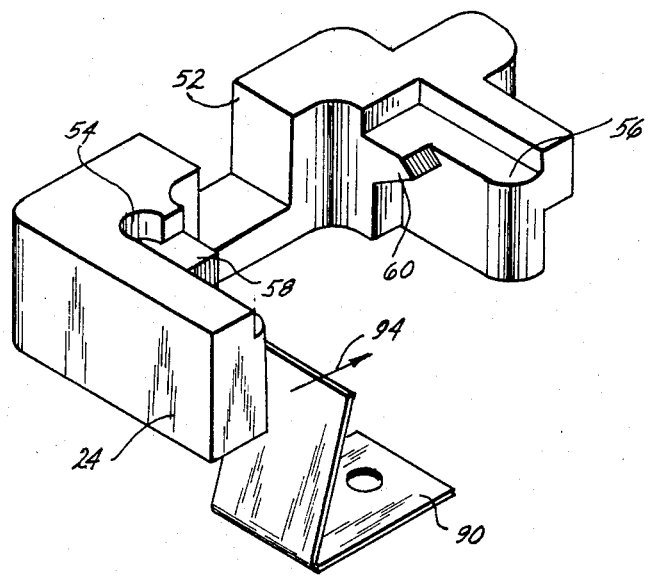
FIG. 3B is a perspective view of the lower hinge bracket of the present invention.

As shown in FIG. 2, lower hinge braket 24 is mounted to the front of the device 10. A more detailed description of lower hinge bracket 24 and its structure for the present invention is, however, best appreciated with reference to FIG. 3B. As shown in FIG. 3B, the lower hinge bracket 24 is formed with a yoke 52. Also formed on lower hinge bracket 24 is a recess 54 adapted for mating engagement with key 38 of slide clamp fitment 20. Additionally, lower hinge bracket 24 is formed with a platform 56 and a platform 58 which are adapted to respectively urge against tab 34 and tab 36 of slide clamp fitment 20. Also shown in FIG. 3B is sear 60 which is formed on lower hinge bracket 24.

The cooperation of structure between slide clamp assembly 30 and lower hinge bracket 24 is shown by the combination of these components in FIG. 4 or FIG. 5. In cross-referencing FIG. 3B with FIG. 4 or FIG. 5, it will be appreciated that the slide clamp fitment 20 of slide clamp assembly 30 nests in lower hinge bracket 24. It will further be appreciated that the mating engagement of key 38 with recess 54 can only be accomplished upon a specific orientation of slide clamp fitment 20 with respect to lower hinge bracket 24. This requirement for specific orientation of key 38 with recess 54 is a safety feature which prevents an inadvertent mating of slide clamp fitment 20 with lower hinge bracket 24 in an inoperable condition.

Grip 64, which is shown by itself in FIG. 6, includes a pair of hooks 66a and 66b which straddle the channel 74 formed on grip 64. Also formed on grip 64 is a sear cam 68 and a pivot 70. It is to be appreciated that grip 64 is pivotally attached to handle 72 at pivot 70 as shown in FIG. 2. A spring bias (not shown) urges grip 64 in the direction opposite to that indicated by the arrow 78 and into its position relative to door 72 substantially as shown in FIG. 2. Impliedly, grip 64 can be rotated around pivot 70 in the direction indicated by arrow 78 but the spring bias tends to restore grip 64 into the position shown in FIG. 2.

Figures 7A, 7B:
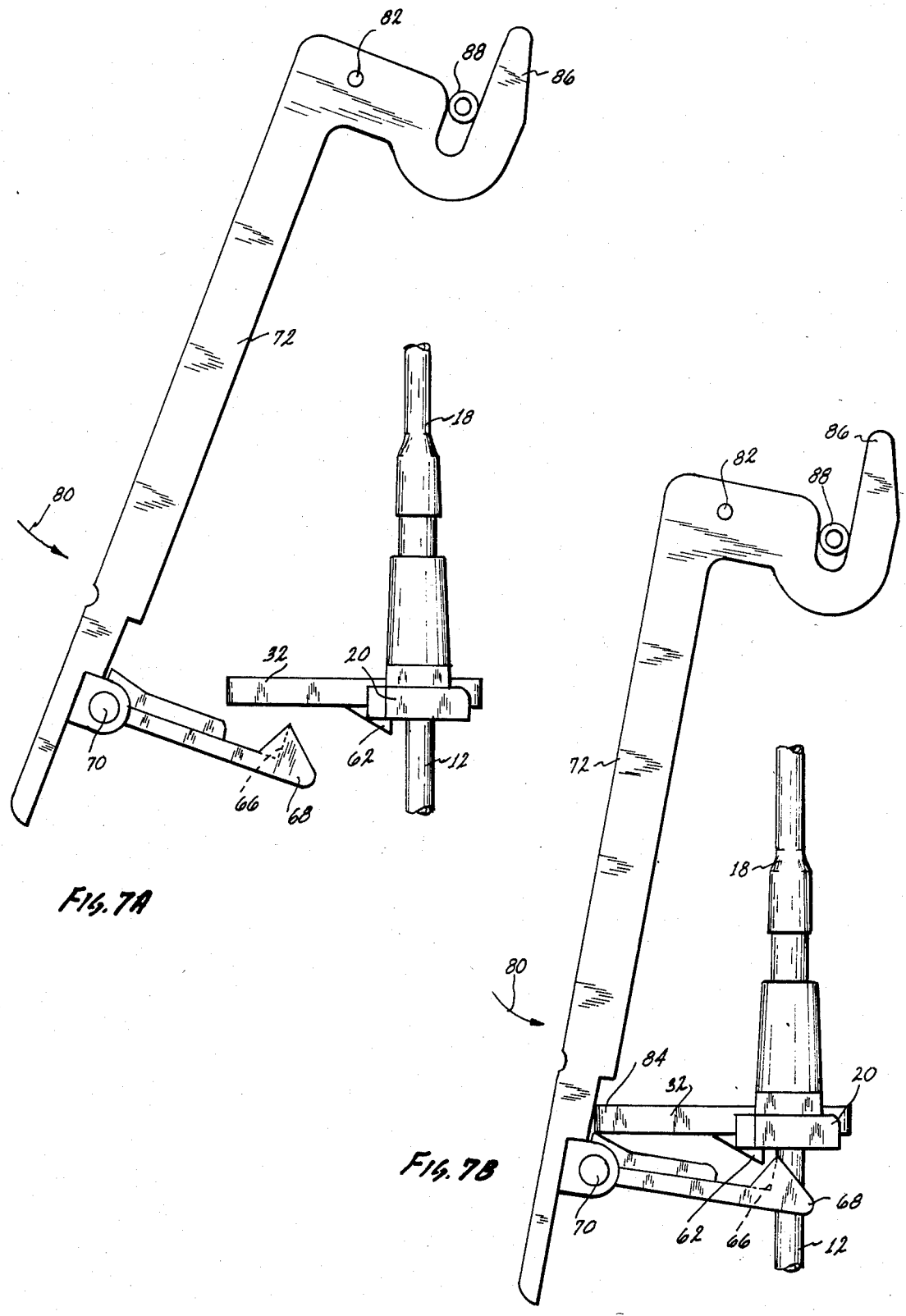
FIG. 7A is an elevation view of the handle and slide clamp assembly in a disengaged configuration with portions of structure omitted for clarity.
FIG. 7B is a view of the handle and slide clamp assembly as shown in FIG. 7A in a partially engaged configuration with portions of structure omitted for clarity.
Figures 7C, 7D:
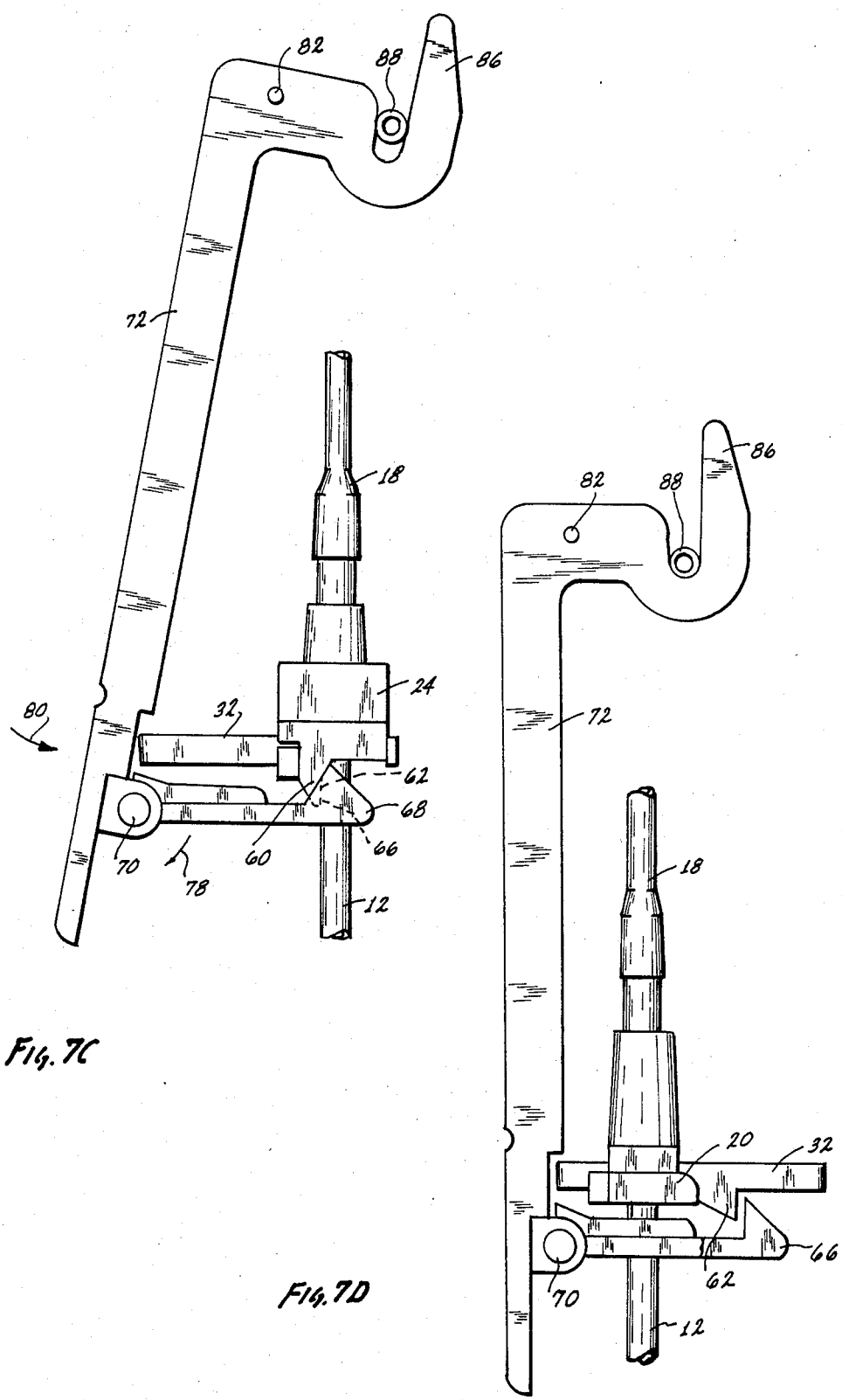
FIG. 7C is a view of the handle and slide clamp assembly as shown in FIG. 7A engaged with the slide clamp closed on the IV tube with portions of structure omitted for clarity.
FIG. 7D is a view of the handle and slide clamp assembly as shown in FIG. 7A engaged with the slide clamp positioned for an open IV tube with portions of structure omitted for clarity.

To consider the cooperation of structure between handle 72, its associated grip 64 and slide clamp assembly 30, it should be appreciated that the closure of door 76 onto device 10 places handle 72 relative to slide clamp assembly 30 as shown in FIGS. 7A, 7B, 7C and 7D. These figures need to be considered sequentially. In FIG. 7A it can be appreciated that the handle 72 is rotatably attached to door 76 (not shown in FIG. 7A) at a pivot point 82. Rotation of handle 72 about pivot 82 in the direction of arrow 80 brings both handle 72 and grip 64 into initial contact with slide clamp 32 as shown in FIG. 7B. The comparision of FIG. 7B with FIG. 7A shows that when in the position shown in FIG. 7B, hooks 66a and 66b of grip 64 make contact with projections 62a and 62b of slide clamp 32 and are urged to rotate grip 64 about pivot 70 in the direction shown by arrow 78 in FIG. 2. Further, and more specifically, movement of handle 72 from its position in FIG. 7A to FIG. 7B causes handle 72 to contact end portion 84 of slide clamp 32. A slightly further rotation of handle 72 in the direction of arrow 80 about pivot point 82 causes hooks 66a and 66b to engage with projections 62a and 62b as shown in FIG. 7C. Specifically, cross-referencing FIG. 7B with FIG. 7C shows that the movement of handle 72 into its position as shown in FIG. 7C causes grip 64 to ride over the projections 62a and 62b of slide clamp 32 and allow the spring biased grip 64 to move into its position as shown in FIG. 7C.

The relation of slide clamp 32 to slide clamp assembly 30, as shown in FIG. 7C, corresponds to the configuration of slide clamp assembly 30 as shown in FIG. 4. Thus, as seen in FIG. 7C, IV tube 12 is still restricted and complete engagement of the handle 72 with device 10 has not yet been accomplished. Further rotation of handle 72 in the direction of arrow 80 brings handle 72 into position with slide clamp 32 as shown in FIG. 7D.

FIG. 7D shows the locked engagement which results by closing door 76 on device 10. The lock is accomplished by bringing latch extension 86 of handle 72 into position relative to anchor pin 88. As best seen in FIG. 2, anchor pin 88 is fixedly attached to device 10. It can be appreciated that the rotation of handle 72 in the direction of arrow 80, as shown sequentially in FIGS. 7A, 7B, 7C and 7D, wraps latch extension 86 around anchor pin 88 to lock door 76 against the device 10. This locking accomplishes several purposes. Importantly, it positions door 76 against pumping section 18 for the purpose of acting as a platen in the peristaltic action of peristaltic pumping means 28. Additionally, when locked on device 10, door 76 protects the engagement of fitments 20 and 22 with their respective brackets 24 and 26.

An important safety feature of the present invention can be appreciated by cross-referencing FIG. 2 with FIG. 3B. Both FIG. 2 and FIG. 3B show a lockout spring 90. It is to be understood that in its unbiased position, lockout spring 90 is positioned to prevent the movement of slide clamp 32 from the position as shown in FIG. 4 to a position as shown in FIG. 5 when slide clamp assembly 30 is joined to lower hinge bracket 24. However, as door 76 is closed onto device 10, a pin 92 which is attached to door 76 as shown in FIG. 2 makes contact with lockout spring 90 and bends it in the direction of arrow 94 to allow the sliding movement of slide clamp 32 past lockout spring 90. Thus, with lockout spring 90 cleared from the path of slide clamp 32, slide clamp 32 is capable of being moved from a position as shown in FIG. 4 to the position shown in FIG. 5.

It should be appreciated that the disengagement of IV tube 12 from the device 10 can be accomplished by reversal of the steps previously discussed and that the cooperation of structure between grip 64 and slide clamp 32 would be substantially as shown by sequentially considering FIGS. 7D, 7C, 7B and 7A. Further, it should be appreciated that as door 76 is unlocked by the movement of handle 72, slide clamp 32 is repositioned to constrict IV tube 12. Accordingly, the removal of IV tube 12 from device 10 can only be accomplished when IV tube 12 is constricted to prevent fluid flow therethrough.

OPERATION

For its operation the present invention requires that IV tube 12 be engaged with peristaltic device 10. This is accomplished by positioning fitment 22 on IV tube 12 in upper bracket 26. The pumping section 18 of IV tube 12 is then stretched to allow the positioning of slide clamp fitment 20 into lower hinge bracket 24. This placement of IV tube 12 on device 10 places pumping section 18 of IV tube 12 against peristaltic pumping means 28. The initial engagement of slide clamp fitment 20 with lower hinge bracket 24 positions the slide clamp assembly 30 against lower hinge bracket 24 in the manner shown in FIG. 4. Thus, for its initial engagement the slide clamp 32 is positioned relative to IV tube 12 to constrict and prevent fluid flow therethrough. In both FIG. 2 and FIG. 4, it is seen that the key 38 of slide clamp fitment 20 requires that the engagement of slide clamp fitment 20 with lower hinge bracket 24 be accomplished only as shown in FIG. 4. This places tab 34 and tab 36 respectively against the platforms 56 and 58 of lower hinge bracket 24.

With IV tube 12 positioned against device 10, door 76 can be closed onto device 10. This results in a sequence of operations which will be best appreciated by reference to FIGS. 7A, 7B, 7C and 7D. As the door 76 is closed onto device 10, the latch extension 86 of handle 72 is positioned around anchor pin 88. Additionally, the grip 64 comes into contact with projections 62a and 62b of slide clamp 32. Also, handle 72 makes contact with slide clamp 32 against its end portion 84. Movement of handle 72 in a rotational motion about the pivot point 82 in the direction of arrow 80 causes handle 72 to urge against slide clamp 32 and engage hoods 66a and 66b on grip 64 with the projections 62a and 62b on slide clamp 32. Further movement of handle 72 in the direction of arrow 80, as shown in the progression from FIG. 7B to FIG. 7C, causes the grip 64 to engage with slide clamp 32. Additional movement of handle 72 from its position in FIG. 7C to a position in FIG. 7D causes handle 72 to urge against slide clamp 32 and position slide clamp 32 relative to slide clamp assembly 30 in a position as shown in FIG. 5. Accordingly, when handle 72 has been completely engaged with door 76, IV tube 12 is made patent for the passage of fluid therethrough. Simultaneous with the opening of slide clamp 32 on IV tube 12, the closure of door 76 causes pin 92 to contact lockout spring 90 and bend it in a direction indicated by arrow 94 to allow further motion of the handle 72 against slide clamp 32. As lockout spring 90 is moved out of the way to allow for the movement of handle 72, the sequence of engagement discussed above for FIG. 7A through FIG. 7D is accomplished.

A consideration of FIGS. 7A, 7B, 7C and 7D in reverse order discloses the cooperation of structure required for disengagement of the IV tube 12 from device 10. Specifically, as handle 72 is rotated about pivot point 82 in a direction opposite to arrow 80, the grip 64 is withdrawn in a manner which urges the hooks 66a and 66b against projections 62a and 62b to cause movement of slide 32 from a position relative to IV tube 12 as shown in FIG. 5 to a position for slide clamp 32 relative to IV tube 12 as shown in FIG. 4. It is important that once grip 64 is withdrawn to the position as shown in FIG. 7C, the sear cam 68, which is clearly shown on grip 64 in FIG. 6, rides over sear 60, which is shown in FIGS. 4 and 5 as part of the lower hinge bracket 24, to urge grip 64 in the direction of arrow 78. This motion clears the grip 64 from the projections 62a and 62b of slide clamp 32 and allows for further rotation of handle 72. It will be appreciated that the further rotation of handle 72 is continued until latch extension 86 is cleared from its engagement with anchor pin 88, thus, unlocking door 76 from device 10 and allowing the opening of door 76. Once door 76 has been opened, the IV tube 12 can be removed from its fittings with device 10 and used as desired by the operator. It will be apreciated that the action of grip 64 in opening door 76 has caused slide clamp 32 to constrict upon IV tube 12 and prevent fluid flow through IV tube 12 upon the removal of IV tube 12 from the device 10.

While the IV tube activator has herein shown and disclosed in detail is fully capable of obtaining the object and providing the advantages herein before stated, it is to be understood that it is merely illustrative of the presently preferred embodiment of the invention and that no limitations are intended to the details of construction or design herein shown other than as defined in the appended claims.

I claim:

1. An apparatus for engaging an IV tube with a device used to infuse medical solutions to a patient which comprises:
   a rigid clamp having relatively fixed clamping surfaces engageable with said IV tube and moveable relative to said tube between an open position wherein fluid can flow through said tube and a closed position wherein said tube is occluded by said clamp;
   means for holding said IV tube in operative engagement with said device;
   lockout means mounted on said device to establish said clamp in said closed position before operative engagement of said IV tube with said device; and
   a handle associated with said device and moveable for engagement with said clamp to urge said clamp between said open position and said closed position.

2. An apparatus as cited in claim 1 which further comprises:
   means associated with said device to disengage said lockout means and allow engageable movement of said handle with said clamp.

3. An apparatus as cited in claim 2 wherein a section of said IV tube has a first end and a second end and is made of a stretchable material.

4. An apparatus as cited in claim 3 wherein said IV tube further comprises:
   a first fitment associated with said first end;
   a second fitment associated with said second end; and
   said holding means comprises a first bracket for engageably receiving said first fitment and a second bracket spaced from said first bracket for engageably receiving said second fitment to stretch said section between said first and second brackets.

5. An apparatus as cited in claim 4 wherein said clamp is formed with a projection and said handle has a hook engageable with said projection to urge said clamp from said open position to said closed position.

6. An apparatus as cited in claim 5 further comprising:
   a door hingedly mounted on said device for enclosing said IV tube between said door and said device when said door is closed.

7. An apparatus as cited in claim 6 wherein said handle is mounted on said door and said lockout disengaging means is mounted on said door.

8. A tube restrictior which comprises:
   a base;
   a rigid clamp having relatively fixed clamping surfaces slidably mountable on said base having a first end and a second end and formed with a generally tear-drop shaped aperture having its wide portion adjacent said first end and its narrow portion adjacent said second end;
   a projection extending from said clamp;
   a tube extending through said aperture;
   a first means mounted on said base for urging against said first end to position said tube in said wide portion of said aperture and allow fluid flow through said tube;
   a second means mounted on said first means for urging against said projection to position said tube in said norrow portion of said aperture and occlude said tube; and
   a lockout means mounted on said base to position said tube in said narrow portion of said aperture upon initial mounting of said clamp on said base.

9. A tube restrictor as cited in claim 8 wherein said base is a device used for the infusion of medical solutions to a patient.

* * * * *